United States Patent
Estevez et al.

(10) Patent No.: US 10,610,237 B2
(45) Date of Patent: Apr. 7, 2020

(54) USER ACTUATED RELOADABLE CLIP CARTRIDGE

(71) Applicant: BOSTON SCIENTIFIC SCIMED, INC., Maple Grove, MN (US)

(72) Inventors: Ramon Estevez, Lowell, MA (US); Shawn Ryan, Littleton, MA (US); John Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 15/801,075

(22) Filed: Nov. 1, 2017

(65) Prior Publication Data

US 2018/0116677 A1 May 3, 2018

Related U.S. Application Data

(60) Provisional application No. 62/417,026, filed on Nov. 3, 2016.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/1222* (2013.01); *A61B 17/1227* (2013.01); *A61B 2017/0053* (2013.01); *A61B 2017/00292* (2013.01); *A61B 2017/00477* (2013.01); *A61B 2017/00818* (2013.01);
(Continued)

(58) Field of Classification Search
CPC . A61B 17/122; A61B 17/1227; A61B 17/128; A61B 17/1285
See application file for complete search history.

(56) References Cited

U.S. PATENT DOCUMENTS

| | | | |
|---|---|---|---|
| 7,452,327 B2 * | 11/2008 | Durgin | A61B 17/122 600/104 |
| 8,062,311 B2 * | 11/2011 | Litscher | A61B 17/122 606/143 |

(Continued)

FOREIGN PATENT DOCUMENTS

| EP | 2371303 | 10/2011 |
|---|---|---|
| EP | 3023061 | 5/2016 |
| WO | 2006/062020 | 6/2006 |

*Primary Examiner* — Ryan J. Severson
(74) *Attorney, Agent, or Firm* — Fay Kaplun & Marcin, LLP

(57) ABSTRACT

A system for treating tissue includes an applicator and a clip assembly. The applicator includes a catheter extending longitudinally and a lumen extending therethrough, a control member extending through the lumen of the catheter. The assembly is releasably coupleable to a distal end of the applicator. The assembly includes a pair of clip arms, proximal ends of which are slidably received within a channel of a capsule, a pair of opposing coupling elements extending proximally from the proximal ends of the arms to be fixed over the distal end of the member so that the arms are movable relative to the capsule via a longitudinal motion of the member between a tissue receiving configuration, in which distal ends of the arms are separated from one another, and a tissue clipping configuration, in which distal ends of the arms are moved toward one another.

19 Claims, 6 Drawing Sheets

(51) Int. Cl.
*A61B 17/00* (2006.01)
*A61B 90/00* (2016.01)
*A61B 17/12* (2006.01)

(52) U.S. Cl.
CPC ........... *A61B 2017/00862* (2013.01); *A61B 2017/00946* (2013.01); *A61B 2017/12004* (2013.01); *A61B 2090/034* (2016.02); *A61B 2090/037* (2016.02)

(56) References Cited

U.S. PATENT DOCUMENTS

| | | | |
|---|---|---|---|
| 8,083,668 B2 * | 12/2011 | Durgin | A61B 17/122 600/104 |
| 8,114,098 B2 * | 2/2012 | Kimura | A61B 10/04 606/139 |
| 8,152,824 B2 * | 4/2012 | Kimura | A61B 17/1222 606/157 |
| 8,157,824 B2 * | 4/2012 | Kimura | A61B 17/1222 606/157 |
| 8,348,964 B2 * | 1/2013 | Kimura | A61B 17/1222 606/157 |
| 8,444,660 B2 * | 5/2013 | Adams | A61B 17/122 606/157 |
| 8,491,610 B2 * | 7/2013 | Karpiel | A61B 17/083 606/142 |
| 8,551,119 B2 * | 10/2013 | Kogiso | A61B 17/122 606/142 |
| 8,663,247 B2 * | 3/2014 | Menn | A61B 17/122 606/142 |
| 8,685,048 B2 * | 4/2014 | Adams | A61B 17/122 606/157 |
| 8,690,899 B2 * | 4/2014 | Kogiso | A61B 17/122 606/142 |
| 8,709,027 B2 * | 4/2014 | Adams | A61B 17/122 606/157 |
| 8,764,774 B2 * | 7/2014 | Sigmon, Jr. | A61B 17/122 24/535 |
| 8,974,371 B2 * | 3/2015 | Durgin | A61B 17/122 600/104 |
| 9,072,520 B2 * | 7/2015 | Terada | A61B 17/1222 |
| 9,084,604 B2 * | 7/2015 | Litscher | A61B 17/122 |
| 9,271,731 B2 * | 3/2016 | Adams | A61B 17/122 |
| 9,332,988 B2 * | 5/2016 | Adams | A61B 17/122 |
| 9,370,371 B2 * | 6/2016 | Durgin | A61B 17/122 |
| 9,743,933 B2 * | 8/2017 | Phillips-Hungerford | A61B 17/1285 |
| 9,980,725 B2 * | 5/2018 | Durgin | A61B 17/122 |
| 10,010,336 B2 * | 7/2018 | Martinez | A61B 17/08 |
| 10,143,479 B2 * | 12/2018 | Adams | A61B 17/122 |
| 10,172,623 B2 * | 1/2019 | Adams | A61B 17/122 |
| 10,172,624 B2 * | 1/2019 | Adams | A61B 17/122 |
| 2002/0045909 A1 * | 4/2002 | Kimura | A61B 17/083 606/151 |
| 2002/0151916 A1 * | 10/2002 | Muramatsu | A61B 17/1227 606/158 |
| 2003/0069592 A1 * | 4/2003 | Adams | A61B 17/122 606/142 |
| 2005/0182426 A1 * | 8/2005 | Adams | A61B 17/122 606/142 |
| 2006/0271066 A1 * | 11/2006 | Kimura | A61B 10/04 606/108 |
| 2011/0112551 A1 * | 5/2011 | Adams | A61B 17/122 606/142 |
| 2011/0238093 A1 * | 9/2011 | Matsuoka | A61B 17/1285 606/151 |
| 2012/0065646 A1 * | 3/2012 | Phillips-Hungerford | A61B 17/1285 606/142 |
| 2013/0006273 A1 * | 1/2013 | Adams | A61B 17/122 606/142 |
| 2013/0231685 A1 * | 9/2013 | Adams, Jr. | A61B 17/122 606/142 |
| 2013/0231686 A1 * | 9/2013 | Adams, Jr. | A61B 17/122 606/142 |
| 2014/0249551 A1 * | 9/2014 | Adams | A61B 17/122 606/142 |
| 2014/0257342 A1 * | 9/2014 | Adams | A61B 17/122 606/142 |
| 2014/0379018 A1 * | 12/2014 | Martinez | A61B 17/08 606/185 |
| 2016/0128698 A1 * | 5/2016 | Adams | A61B 17/122 606/142 |
| 2016/0143644 A1 * | 5/2016 | Adams | A61B 17/122 606/142 |
| 2016/0213378 A1 * | 7/2016 | Adams | A61B 17/122 |
| 2017/0325823 A1 * | 11/2017 | Phillips-Hungerford | A61B 17/1285 |
| 2018/0078261 A1 * | 3/2018 | King | A61B 17/122 |
| 2018/0078262 A1 * | 3/2018 | Lehtinen | A61B 17/1227 |
| 2018/0085122 A1 * | 3/2018 | Ryan | A61B 17/10 |
| 2018/0098771 A1 * | 4/2018 | King | A61B 17/122 |
| 2018/0116677 A1 * | 5/2018 | Estevez | A61B 17/1285 |
| 2018/0153552 A1 * | 6/2018 | King | A61B 17/083 |

* cited by examiner

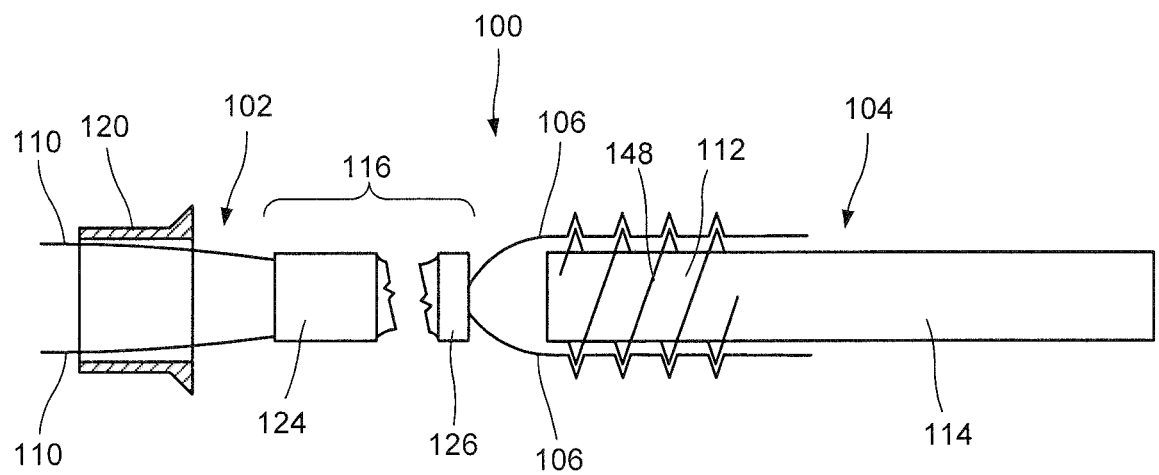
F I G. 5
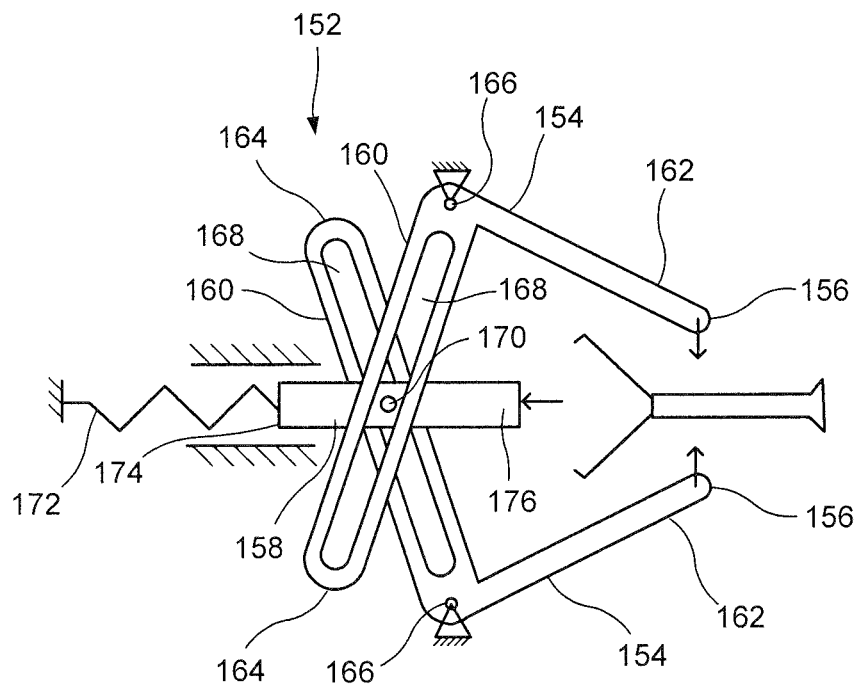
F I G. 6

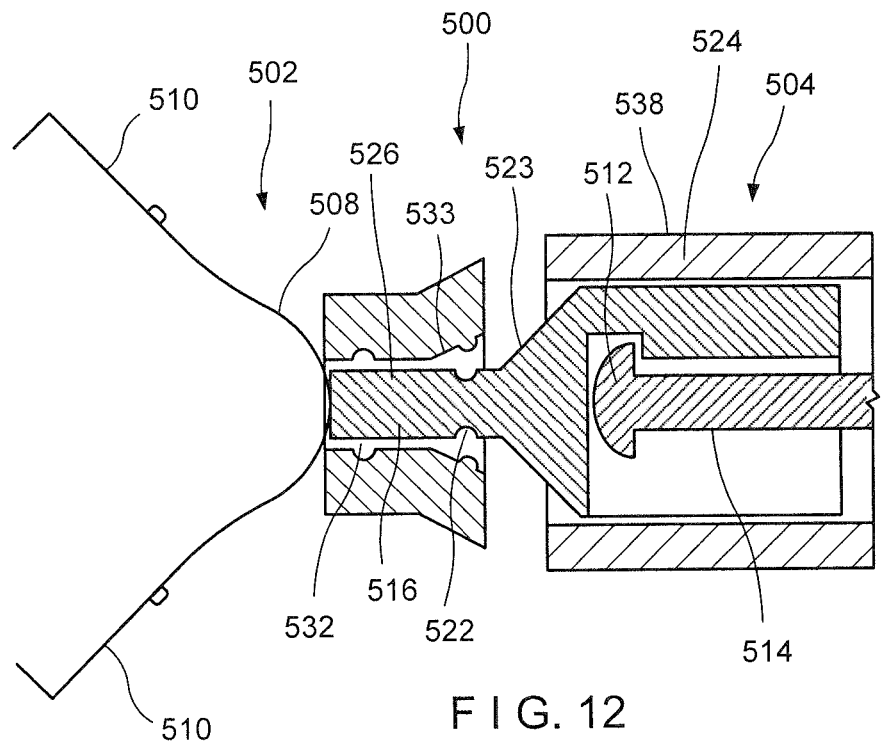
F I G. 12
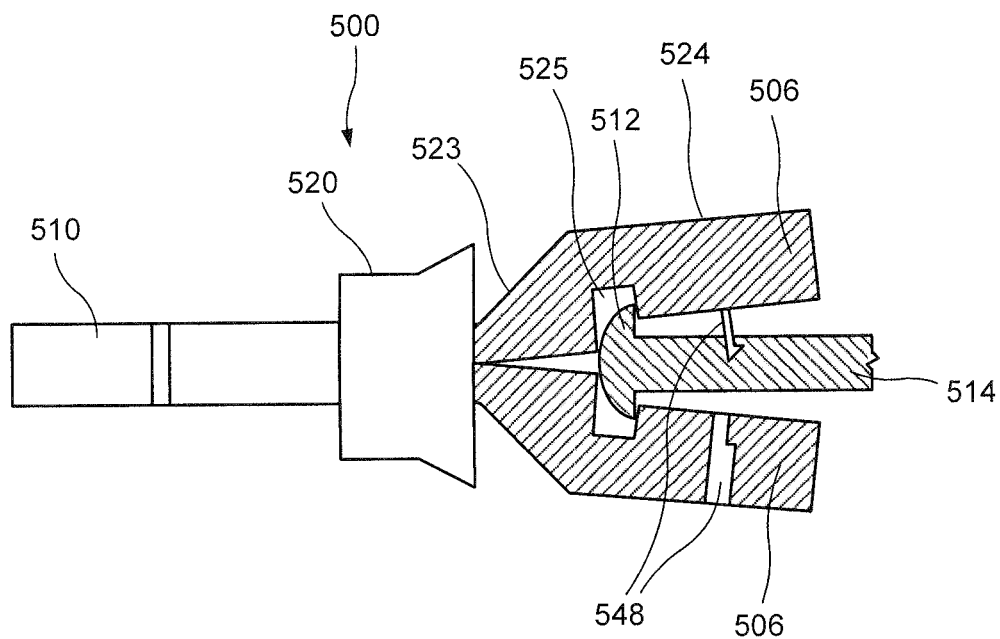
F I G. 13

USER ACTUATED RELOADABLE CLIP CARTRIDGE

PRIORITY CLAIM

This present disclosure claims priority to U.S. Provisional Patent Application Ser. No. 62/417,026 filed Nov. 3, 2016; the disclosure of which is incorporated herewith by reference.

BACKGROUND

Pathologies of the gastrointestinal (GI) system, the biliary tree, the vascular system, and other body lumens and hollow organs are often treated through endoscopic procedures, many of which require hemostasis to control internal bleeding. Hemostasis clips grasp tissue surrounding a wound and hold edges of the wound together temporarily to allow natural healing processes to permanently close the wound. Specialized endoscopic clipping devices are used to deliver the clips at the desired locations within the body after which the clip delivery device is withdrawn, leaving the clip within the body.

SUMMARY

The present disclosure relates to a system for treating tissue, comprising an applicator including a catheter extending longitudinally from a proximal end to a distal end and including a lumen extending therethrough, a control member extending through the lumen of the catheter and a clip assembly releasably coupleable to a distal end of the applicator, the clip assembly including a pair of clip arms, proximal ends of which are slidably received within a channel of a capsule, a pair of opposing coupling elements extending proximally from the proximal ends of the clip arms to be fixed over the distal end of the control member so that the clip arms are movable relative to the capsule via a longitudinal motion of the control member between a tissue receiving configuration, in which distal ends of the clip arms are separated from one another, and a tissue clipping configuration, in which distal ends of the clip arms are moved toward one another.

In an embodiment, the pair of opposing coupling elements may be a pair of malleable sheets crimped over the distal end of the control member.

In an embodiment, the distal end of the control member may include a threading extending therealong.

In an embodiment, the proximal ends of the clip arms may be connected to one another via a connector including a proximal portion and distal portion connected to one another via a frangible link designed to fail when a predetermined threshold force is exerted thereon, the malleable element extending proximally from the proximal portion.

In an embodiment, the frangible link may be configured as a notch extending about the connector between the proximal and distal portions.

In an embodiment, a proximal end of the capsule may be releasably coupleable to a distal end of the catheter.

In an embodiment, the proximal end of the capsule may include a protrusion extending laterally outward from an exterior surface thereof and the distal end of the catheter includes a correspondingly sized and shaped recess extending along an interior surface of the lumen, the protrusion configured to be snap fit in the recess.

In an embodiment, the clip arms may be biased in the tissue receiving configuration so that, when the clip arms are drawn proximally into the capsule, an interior surface of the capsule constrains the clip arms toward the tissue gripping configuration.

In an embodiment, the system may further comprise a cartridge defining a space therewithin for housing the clip assembly.

In an embodiment, the cartridge may include a crimping mechanism including crimping members coupled to the cartridge so that a portion of the crimping members are movable toward one another to crimp the opposing coupling elements over the control member.

In an embodiment, the space of the cartridge may be defined via a tapered surface engaging the opposing coupling elements when the clip assembly is moved distally relative thereto so that the opposing coupling elements are moved toward the control member to be crimped thereover.

In an embodiment, the pair of opposing coupling elements may define a space sized and shaped to receive an enlarged distal end of the control member, the opposing coupling elements movable between a non-engaging configuration, in which the opposing coupling elements are separated from one another to receive the enlarged distal end therebetween, and an engaging configuration, in which the opposing coupling elements are moved toward one another to fix the enlarged distal end therein, the pair of opposing coupling elements including corresponding snap features for releasably locking the opposing coupling elements in the engaging configuration.

In an embodiment, the capsule may include an angled surface along a proximal end of the channel, the angled surface configured to interface with tapered surfaces of the opposing coupling elements to move the opposing coupling elements from the non-engaging configuration toward the engaging configuration.

The present disclosure also relates to a system for treating tissue, comprising an applicator including a bushing and a control member extending therethrough, the bushing including an engagement feature at a distal end thereof and a clip assembly releasably coupleable to a distal end of the applicator, the clip assembly including a pair of clip arms, proximal ends of which are slidably received within a channel of a capsule, proximal ends of the clip arms configured to be connected to a distal end of the control member and a proximal end of the capsule configured to be crimped over the engagement feature of the bushing so that the clip arms are movable relative to the capsule between a tissue receiving configuration, in which distal ends of the clip arms are separated from one another, and a tissue clipping configuration, in which distal ends of the clip arms are moved toward one another, via a longitudinal motion of the control member relative to the bushing.

In an embodiment, the proximal ends of the clip arms may be connected to one another via a yoke including a socket sized and shaped to releasably receive an enlarged distal end of the control member.

The present disclosure also relates to a method for treating tissue, comprising loading a first clip assembly on an applicator by coupling a control member of the applicator to proximal ends of clip arms of the first clip assembly by crimping a malleable element connected to the proximal ends of the clip arms over a threaded distal end of the control member and by coupling a catheter of the applicator to a proximal end of a capsule of the first clip assembly, inserting the loaded first clip assembly to a target site within a living body via a working channel of an endoscope, moving the clip assembly between a tissue receiving configuration, in which distal ends of the clip arms are separated from one another, and a tissue clipping configuration, in which distal ends of the clip arms are moved toward one another, by moving the control member longitudinally relative to the locking sleeve until a target tissue is gripped therebetween, as desired, and releasing the first clip assembly from the applicator by drawing the control member proximally relative to the first clip assembly, beyond a predetermined threshold value, so that the malleable element separates from the proximal end of the clip arms.

BRIEF DISCLOSURE

FIG. 5 shows a longitudinal side view of the system of FIG. 1, during deployment of the clip assembly;

FIG. 6 shows a side view of a crimping mechanism for crimping a portion of the crimp assembly over a portion of the applicator, according to the system of FIG. 1;

FIG. 12 shows a partially cross-sectional longitudinal side view of a system according to yet another exemplary embodiment of the present disclosure; and FIG. 13 shows another longitudinal side view of the system of FIG. 12.

DETAILED DESCRIPTION

Figure 1:
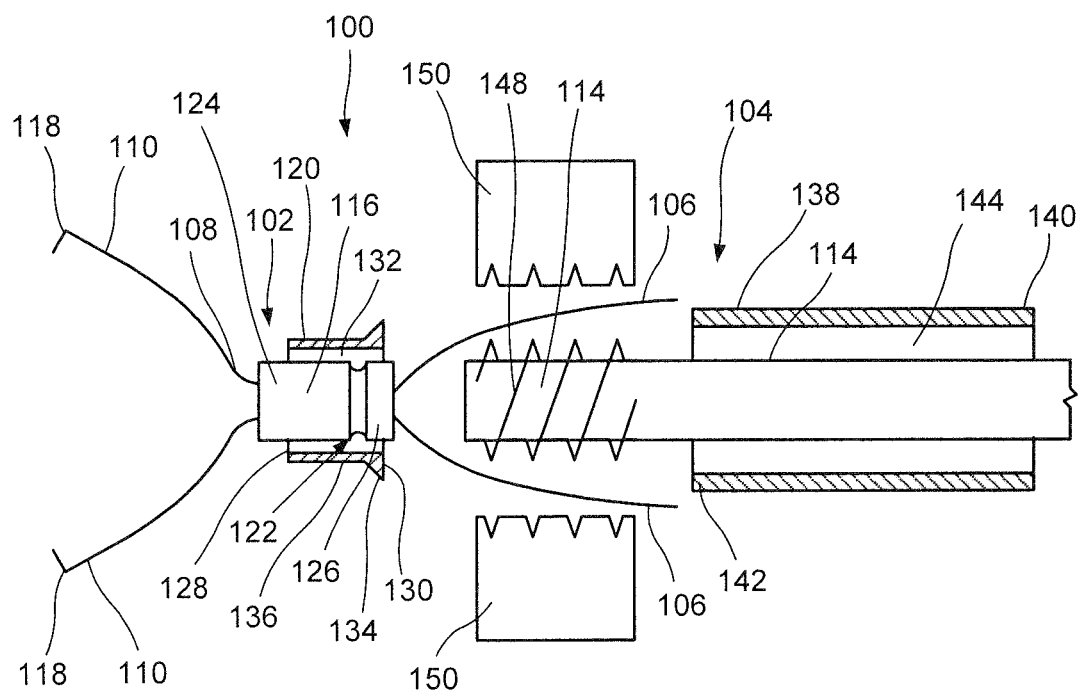
FIG. 1 shows a partially cross-sectional longitudinal side view of a system according to an exemplary embodiment of the present disclosure.

The present disclosure may be further understood with reference to the following description and the appended drawings, wherein like elements are referred to with the same reference numerals. The present disclosure relates to a clipping system and, in particular, relates to a reloadable endoscopic clipping system. Exemplary embodiments of the present disclosure describe a clip assembly that may be loaded onto a distal end of an applicator assembly prior to an endoscopic procedure. Once a clip has been deployed at a desired target area in the body, the applicator assembly may be reloaded with a new clip. In particular, a portion of the clip assembly may be formed of a malleable material which may be crimped over a portion of the applicator to releasably couple the clip assembly thereto. It should be noted that the terms "proximal" and "distal," as used herein, are intended to refer to a direction toward (proximal) and away from (distal) a user of the device.

As shown in FIGS. 1-5, a system 100 according to an exemplary embodiment of the present disclosure comprises a clip assembly 102 loadable onto a distal portion of an applicator 104 prior to insertion of the system 100 into a living body for the clipping of target tissue. The applicator 104 is configured such that, after deployment of the clip assembly 102 in the living body, a new clip assembly 102 may be loaded onto the applicator 104 so that the same applicator 104 may be used to deliver a new clip assembly 102 to a second portion of target tissue in the living body. In particular, the clip assembly 102 includes a malleable element 106 extending proximally from a proximal portion of the clip assembly 102 so that the malleable element 106 is crimpable over a distal end 112 of a control member 114 of the applicator 104. Thus, the malleable element 106 couples the clip assembly 102 to the control member 114 so that the clip assembly 102 may be moved proximally and distally to move the clip arms 110 between an open, tissue receiving configuration and a closed, tissue gripping configuration, as will be described in further detail below.

The clip assembly 102 includes a pair of clip arms 110, proximal ends 108 of which are, in this embodiment, connected to one another via a connector 116 that is slidably received within a capsule 120. The clip arms 110 of this embodiment are biased so that distal ends 118 thereof move apart from one another into the open, tissue receiving configuration when not drawn proximally into the capsule 120. When they are drawn into the capsule 120, the capsule 120 constrains the clip arms 110, holding the distal ends 118 thereof together in the closed, tissue clipping configuration. The connector 116 is longitudinally slidable within the capsule 120 to move the clip arms 110 between the tissue receiving configuration and the tissue gripping configuration.

Each of the clip arms 110 extends from a proximal end 108 to a distal end 118. The distal end 118 of each of the clip arms 110 in this embodiment projects laterally inward toward the distal end 118 of the other of the clip arms 110 to facilitate gripping of target tissue therebetween. The distal ends 118 may further include other gripping features such as, for example, teeth and/or protrusions. The clip arms 110 may also include a locking feature configured to lock the clip arms 110 in the tissue gripping configuration, once target tissue has been gripped via the clip arms 110. In one embodiment, the clip arms 110 may include a locking tab extending laterally outward therefrom. This locking tab may be configured to engage a portion of the capsule 120 when the clip arms 110 have been drawn into the capsule 120 by a predetermined distance. For example, the locking tabs may be received within correspondingly sized, shaped and positioned locking windows extending laterally into or through a wall of the capsule 120 to lock a position of the clip arms 110 relative to the capsule 120 holding the clip arms 110 in the tissue gripping configuration to securely grip any tissue received between the distal ends 118 of the clip arms 110 and prevent the clip arms 110 from being moved distally out of the capsule 120.

In this embodiment, the proximal ends 108 of the clip arms 110 may be connected to one another via the connector 116, which is configured to be connected to the control member 114 of the applicator 104. The connector 116 includes a separable link configured as, for example, a notch 122 extending thereabout to connect a proximal portion 124 and a distal portion 126 of the connector to one another. The notch 122 is configured to weaken the connector 116 at this position so that it will break, separating the proximal and distal portions 124, 126, when a force exerted thereon exceeds a predetermined threshold value. Although the separable link is shown and described as a notch 122, the separable link may have any of a variety of configurations, so long as the link separates when a force exerted thereon exceeds the predetermined threshold value, thereby separating the proximal and distal portions 124, 126 of the connector 116. For example, rather than a notch 122, a portion of the connector 116 between the proximal and distal portions 124, 126 may be weakened in other ways so that the proximal and distal portions 124, 126 may be separated from one another when a predetermined threshold force is exerted thereon. In another example, the proximal and distal portions 124, 126 may be connected to one another via a weld or other connecting mechanism designed to fails when exerted with a predetermined force.

As described above, the clip arms 110, according to this embodiment, are biased toward the tissue receiving configuration so that, when the connector 116 is drawn proximally into the capsule 120 via the control member 114, an interior surface of the capsule 120 engages at least a portion of each of the clip arms 110 to draw the clip arms 110 together toward the tissue gripping configuration. When the connector 116 is moved distally relative to the capsule 120, the clip arms 110 are moved distally beyond a distal end 128 of the capsule 120, freeing the clip arms 110 to spring apart from one another under their natural bias toward the tissue receiving configuration. When target tissue is positioned between the distal ends 118 as desired, the clip arms 110 are moved locked into the tissue gripping configuration by drawing the control member proximally relative to the capsule 120 until corresponding locking features of the clip arms 110 and the capsule 120 engage one another. To deploy the clip assembly 102 in the body in the locked configuration, the control member 114 may be moved even further proximally until a force exerted on the connector 116 exceeds the predetermined threshold value, causing the notch 122 to break so that the proximal portion 124 of the connector 116 connected to the control member 114 is separated from the distal portion 126 of the connector 116.

Figure 2:
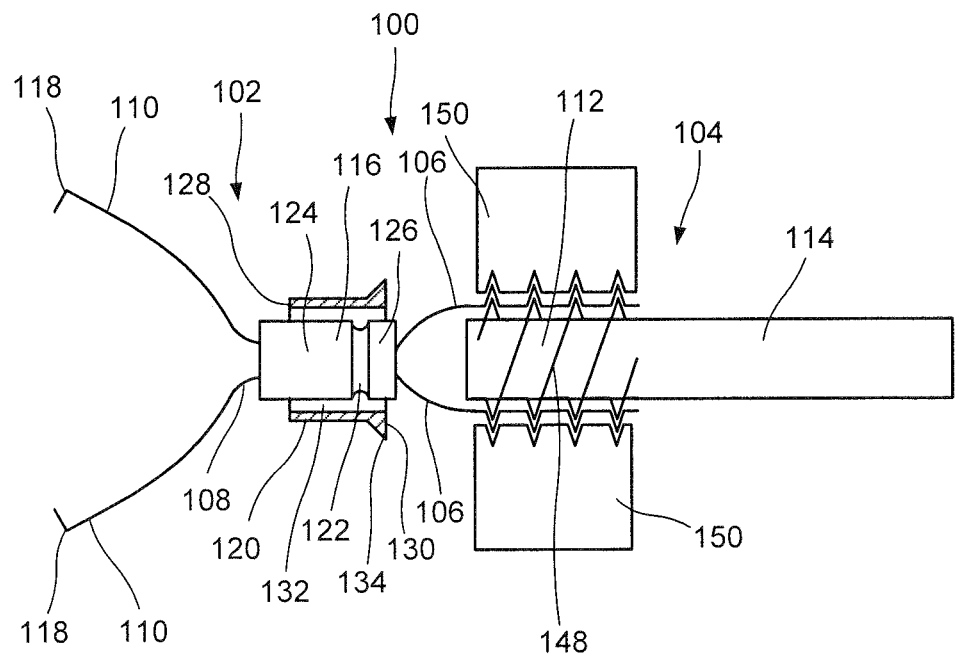
FIG. 2 shows a partially cross-sectional longitudinal side view of the system of FIG. 1, with a malleable element of a clip assembly crimped over a control member.

According to this embodiment, the distal end 112 of the control member 114 is configured to be connected to the connector 116 via the malleable element 106. The malleable element 106 in this embodiment is configured as a one or more malleable sheets extending proximally from the connector 116 (in this case two malleable sheets diametrically opposed to one another). The distal end 112 of the control member 114 is inserted between the pair of malleable sheets, as shown in FIG. 1, so that the malleable sheets may be crimped thereover, as shown in FIG. 2. As will be described in further detail below, the distal end 112 of the control member 114 of this embodiment includes an engaging structure to mechanically interact with the malleable sheets (e.g., a threading 148 extending about the distal end 112, a series of circumferential, or partly circumferential ridges, etc.) so that, when the malleable element 106 is crimped thereover, the malleable element 106 conforms to a shape of the threading 148, thereby locking the connector 116 to the control member 114. The malleable element 106 may be formed of any of a variety of materials (e.g., metals) so long as the material is thin enough to be deformed over the distal end 112 of the control member 114. In one example, the malleable element 106 may be formed of thin sheets of stainless steel.

The malleable sheets may be crimped over the control member 114 via, for example, crimp members 150 positioned on opposing sides of the clip assembly 102 proximate each of the malleable sheets. The crimp members 150 may be sized and shaped to crimp the malleable element 106 over the distal end 112 of the control member 114 in a desired fashion. For example, the crimp member 150 may include a structure corresponding to the engaging structure (threading 148) along the distal end 112 so that, when the crimp members 150 are pressed against the malleable element 106, the malleable element 106 conforms to the shape of the threading 148.

Figure 3:
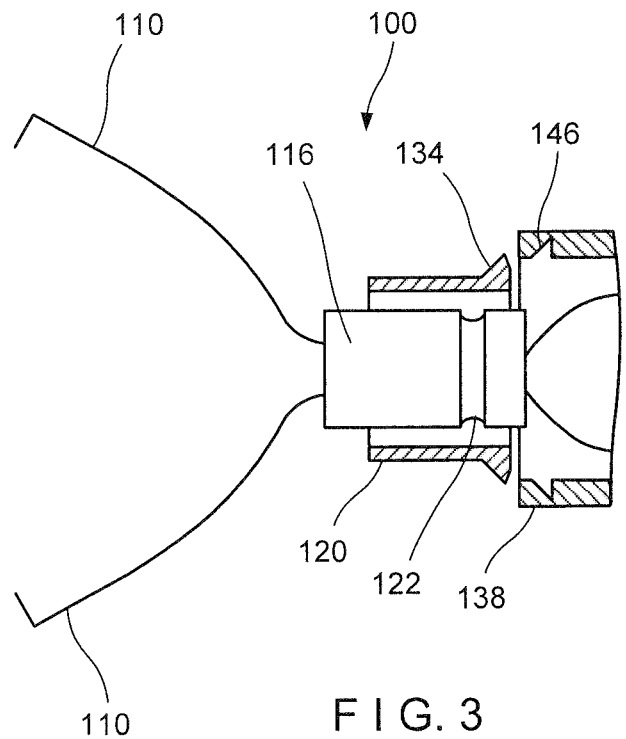
FIG. 3 shows a partially cross-sectional enlarged longitudinal side view of a distal portion of the system of FIG. 1.
Figure 4:
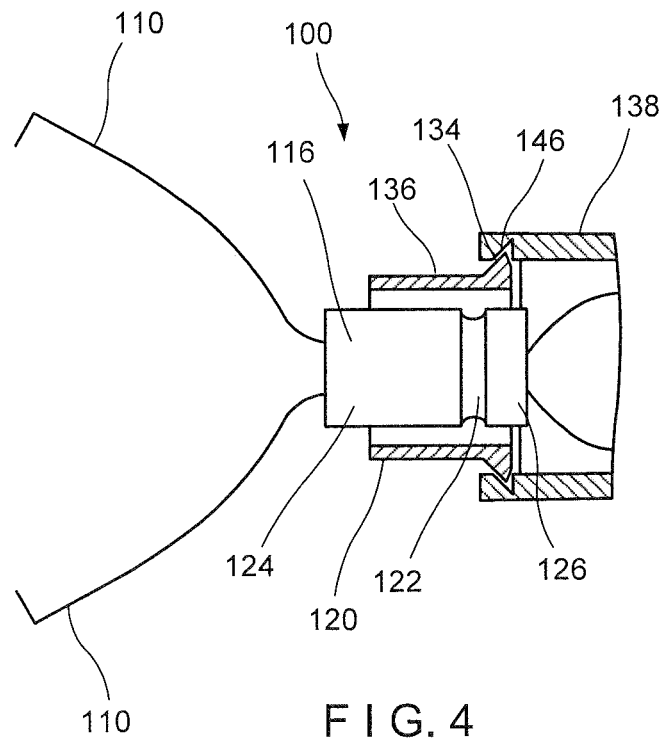
FIG. 4 shows a partially cross-sectional enlarged longitudinal side view of a distal portion of the system of FIG. 1, with a capsule of a clip assembly coupled to a catheter of an applicator.

The capsule 120 extends longitudinally from a proximal end 130 to the distal end 128 and includes a channel 132 extending longitudinally therethrough. The channel 132 is sized and shaped to receive the connector 116 and at least a proximal portion of the clip arms 110. The proximal end 130 of the capsule 120 may be releasably connected to the applicator 104 in any of a variety of ways. In one embodiment, as shown in FIGS. 3-4, the proximal end 130 of the capsule 120 includes an engaging feature configured as, for example, a protrusion 134 extending laterally outward from an exterior surface 136 thereof. The protrusion 134 is configured to releasably engage a corresponding engaging feature of the applicator 104. The capsule 120 and the applicator 104 are engaged so that application of a predetermined distally directed force against the capsule 120 disengages the capsule 120 from the applicator 104. As described above, the capsule 120 may also include features such as, for example, locking windows, for locking the clip arms 110 relative thereto in the tissue gripping configuration.

The applicator 104 includes a catheter 138 and the control member 114 extending therethrough. The catheter 138 may be connected to a distal end of a flexible member (not shown) which connects the catheter 106 to a handle member at a proximal end thereof. The flexible member may be formed, for example, as a coil of wire through which the control member 114 extends. As would be understood by those skilled in the art, the coil of wire preferably has sufficient flexibility to be passed through even tortuous paths of living body and, in this embodiment, is sized and shaped to permit it to be passed through a working channel of a flexible endoscope or other insertion device. Although the flexible member is shown and described as a coil of wire, it will be understood by those of skill in the art that any other suitable flexible structure may be employed so long as the flexible member is capable of providing a force in compression sufficient to counter the tension to be placed on the control member 114 from the clip assembly 102.

The catheter 138 extends longitudinally from a proximal end 140 to a distal end 142 and includes a lumen 144 extending therethrough. The distal end 142 is configured to releasably engage the capsule 120. In one embodiment, the lumen 144 is sized and shaped to receive the capsule 120 therein and may include an engaging feature such as, for example, a recess 146 extending about a distal section thereof, the recess 146 being sized and shaped to receive the protrusion 134 at the proximal end 130 of the capsule 120. The catheter 138 releasably engages the capsule 120 via a loose snap connection so that, longitudinal movement of the control member 114 relative to the catheter 138 moves the clip arms 110 relative to the capsule 120. However, when a distally directed force greater than a predetermined threshold value is exerted on the capsule 120, the capsule 120 disengages from the catheter 138. It will be understood by those of skill in the art, however, that any of a variety of releasable connections between the catheter 138 and the capsule 120 are possible, so long as the capsule 120 may be released from the catheter 138 upon deployment of the clip assembly 102.

The control member 114 extends through the catheter 138 and the flexible member from the distal end 112 to a proximal end, which may be connected to an actuator along the handle member. Thus, the control member 114 may be moved longitudinally with respect to the flexible member and the catheter 138. In one embodiment, the distal end 112 includes a threading 148 extending thereabout so that, when the malleable element 106 is crimped thereover, the malleable element 106 conforms to a shape of the threading 148, locking the malleable element 106 and thereby the clip arms 110 relative to the control member 114. Thus, longitudinal movement of the control member 114 relative to the catheter 138 moves the clip assembly 102 between the tissue receiving and the tissue gripping configurations.

Once target tissue has been gripped via the clip assembly 102 and the clip assembly 102 has been locked in the tissue gripping configuration, the clip assembly 102 may be deployed by drawing the control member 114 proximally relative thereto until the connector 116 of the clip assembly breaks or separates, separating the proximal portion 124 connected to the control member 114 from the distal portion 126 which remains connected to the clip arms 110. Upon withdrawal of the applicator 104 from the body, the proximal portion 124 and the malleable element 106 may be removed from the control member 114 by rotating the malleable element 106 relative thereto. The threading 148 along the distal end 112 permits the malleable element 106 to be threadedly disengaged therefrom so that the same applicator 104 may be loaded with a new clip assembly 102 to clip a second target portion of tissue. Although the control member 114 is described and shown as including the threading 148 at the distal end 112, the distal end 112 may include any of a variety of other features over which the malleable element 106 may be crimped to connect the clip arms 110 to the control member 114.

Prior to being loaded on the applicator 104, the clip assembly 102 may be stored in a cartridge configured to facilitate loading of the clip assembly 102 on the applicator 104. The cartridge may be configured as a storage container defining a space therewithin that is sized and shaped to house the clip assembly 102 with the coupler 106. The clip assembly 102 may be housed within the cartridge in the tissue receiving configuration. The cartridge includes a proximal opening through which the distal portion of the applicator 104 may be inserted to be coupled to the clip assembly 102, as will be described in further detail below. The cartridge holds the clip assembly 102 in position to facilitate loading onto the applicator 104. In particular, the cartridge may hold the clip assembly 102 with the malleable sheets of the malleable element 106 positioned to permit the distal end 112 of the control member 114 to be inserted therebetween.

The cartridge may include a crimping mechanism built thereinto so that the malleable element 106 may be crimped over the distal end 112 via the crimping mechanism thereof. For example, the crimping mechanism may include a linkage system which moves crimping members 150 toward one another to crimp the malleable element 106 over the control member 114 as the applicator 104 pushes the clip assembly 102 against a link. A linkage system 152, as shown in FIG. 6, may include a pair of pivoting sliders 154 positioned on opposing sides of the cartridge so that proximal ends 156 of the sliders 154 may be pressed against the malleable element 106 (e.g., via the crimping members 150) to crimp the malleable element 106 over the control member 114. Each of the sliders 154 may be pivotally connected to the cartridge and slidably connected to one another via linking element 158 so that, when the clip assembly 102 is pressed distally against the linking element 158, the proximal ends 156 are moved toward one another to crimp the malleable element 106.

In particular, each of the sliders 154 of this embodiment includes a distal portion 160 and a proximal portion 162 angled with respect to one another. A distal end 164 of the distal portion 160 of each of the sliders 154 extends toward the proximal end 156 of the proximal portion 162 of the slider 154. The sliders 154 are pivotally connected to the cartridge at a point 166 where the distal and proximal portions 160, 162 meet. The distal portion 160 of each of the sliders 154 includes a slot 168 extending therealong. The distal portions 160 of the sliders 154 are slidably connected to the linking element 158 via a fastener 170 of the linking element 158 which is slidably received within the slots 168 of the sliders 154. The linking element 158 may be substantially axially aligned with the clip assembly 102 and connected to the cartridge via a biasing element such as a spring 172 at a distal end 174 thereof so that, when the clip assembly 102 is pressed distally against a proximal end 176 of the linking element 158, the fastener 170 of the linking element 158 slides distally along the slots 168, causing the sliders 154 to pivot about points 166 moving the proximal ends 156 toward one another. The proximal ends 156 are moved toward one another to crimp the malleable element 106 over the control member 114 via, for example, the crimping members 150.

Figure 7:
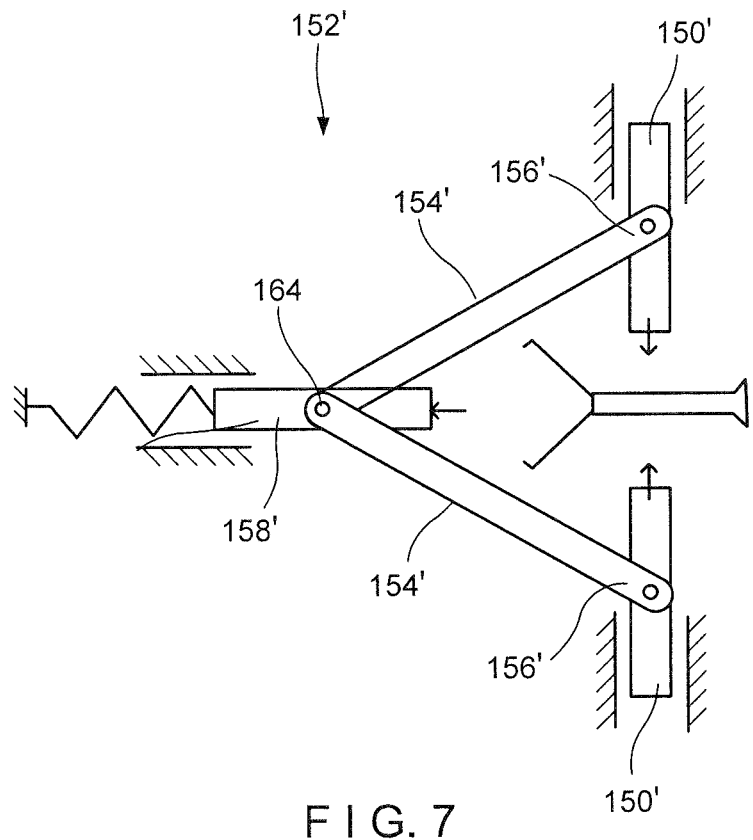
FIG. 7 shows a side view of a crimping mechanism according to an alternate embodiment of the present disclosure.

According to an alternate embodiment, as shown in FIG. 7, a linkage system 152' is substantially similar to the linkage system 152 described above, comprising a pair of sliders 154' connected to one another via a linkage element 158'. The sliders 154', however, do not include angled portions and are pivotally connected to the linkage element at distal ends 164' thereof. Similarly to the linkage system 152', when the linking element 158' is pushed distally via a portion of the clip assembly 102, the sliders are pivoted at the distal ends 164' so that proximal ends 156' thereof are moved toward one another. These proximal ends 156' according to this embodiment are pivotally connected to crimping elements 150' which are moved toward one another to crimp a portion of the clip assembly 102 (e.g., the malleable element 106) positioned therebetween.

Figure 8:
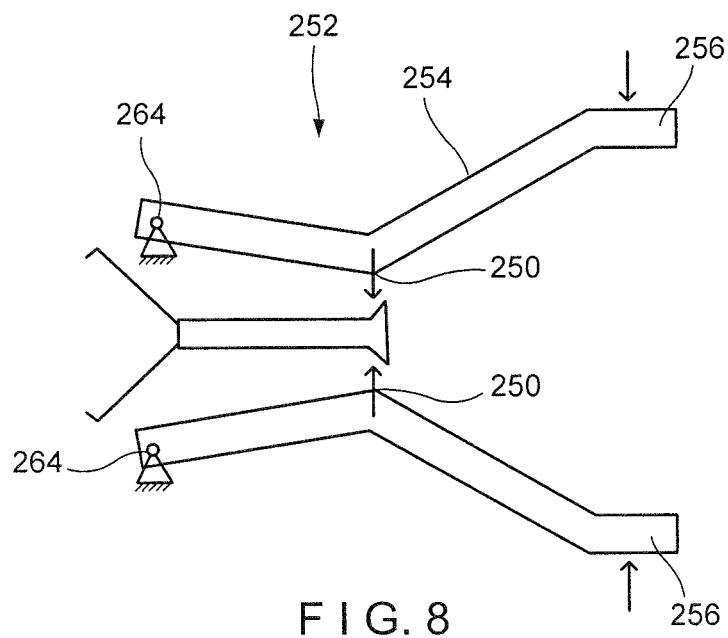
FIG. 8 shows a side view of a crimping mechanism according to another exemplary embodiment of the present disclosure.

As shown in FIG. 8, a crimping mechanism 252 according to another exemplary embodiment comprises a pair of levers 254 pivotally coupled to the cartridge at distal ends 264 thereof. The pair of levers 254 are shaped so that when actuating portions of the levers 254 (e.g., buttons at proximal ends 256 thereof) are pushed toward one another, crimping portions 250 of the levers 254 are pushed against a portion of a clip assembly to crimp a malleable portion thereof over a portion of an applicator. For example, as described above, the crimping portion 250 may crimp the malleable sheets 106 of the clip assembly 102 over the distal end 112 of the control member 114.

Figure 9:
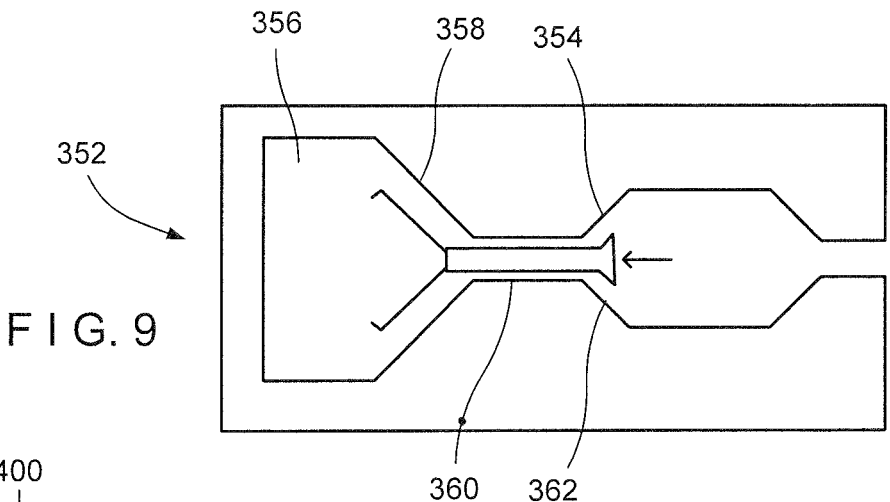
FIG. 9 shows a transparent top view of a cartridge including a crimping mechanism according to yet another exemplary embodiment of the present disclosure.

In yet another embodiment, as shown in FIG. 9, a cartridge 352 for housing a clip assembly according to yet another exemplary embodiment, comprises tapered surface 354 which, when the clip assembly is moved distally thereagainst, causes outwardly extending portions (e.g., malleable sheets 106 of clip assembly 102) to be pushed inward. For example, the cartridge 352 includes a space 356 for housing the clip assembly 102, the space 356 being defined via a distal portion 358, a middle portion 360 and a proximal portion 362. The distal and proximal portions 358, 362 are connected to one another via the middle portion 360. The distal and middle portions 358, 360 are sized and shaped to house the clips arms 110 and the connector 116, respectively. In particular, the distal portion 358 flares distally outward from the middle portion 360 to accommodate the clip arms 110 in the open tissue receiving configuration. The proximal portion 362 flares proximally outward from the middle portion 360 to, for example, accommodate the malleable sheets of the malleable element 306. The proximal portion 362 are defined via the tapered surfaces 354 which taper from a proximal end 364 thereof toward the middle portion 360 so that, when the clip assembly 102 is moved distally with respect to the cartridge 352, the malleable element 306 (or other crimpable portion of a clip assembly) is received within and constrained via the middle portion 360, becoming crimped over a portion (e.g., the control member 114) of the applicator 104.

An exemplary method for loading the clip assembly 102 to the applicator 104 comprises crimping the malleable element 106 over the distal end 112 of the control member 114. The distal end 112 of the control member 114 and the distal end 142 of the catheter 138 may, for example, be inserted into a proximal opening of a cartridge in which the clip assembly is housed so that the distal end 112 is positioned between two malleable sheets of the malleable element 106. Once the distal end 112 has been correctly positioned relative to the malleable element 106, the malleable element 106 may be crimped thereover via crimping elements built into the cartridge to conform malleable element 106 to the shape of the threading 148 extending along the distal end 112 of the control member 114 as described above. The malleable element 106 may be crimped over the distal end of the control member 114 using any of the crimping systems 152, 152', 252 and 352 described above. The control member 114 is this substantially fixed with respect to the clip arms 110. Once the malleable element 106 has been crimped onto the control member 114, the catheter 138 may be moved distally relative to the control member 114 until the distal end 142 of the catheter 138 releasably engages the proximal end 130 of the capsule 120. For example, the protrusion 134 at the proximal end 130 of the capsule may be received within the recess 146 within the lumen 144 of the catheter 138 via a snap fit. To remove the loaded clip assembly 102 from the cartridge, the control member 114 is moved proximally with respect to the catheter 138 to move the clip assembly 102 toward the closed configuration. The entire applicator 104 may then be moved proximally relative to the cartridge to draw the clip assembly 102 out of the cartridge via the proximal opening.

In use, after the clip assembly 102 has been loaded onto the applicator 104, the clip assembly 102 is inserted through a working channel of an endoscope (or any other insertion device) and inserted into the body (e.g., through a natural body lumen) to a site adjacent to a target portion of tissue to be clipped. The clip assembly 102 is inserted to the target tissue in the tissue gripping configuration to reduce damage and facilitate its passage through the working channel. Upon reaching the site of the target tissue, the clip assembly 102 is advanced out of the distal end of the working channel by moving the control member 114 distally relative to the catheter 138 extending the clip arms 110 distally from the capsule 120 and moving the clip arms 110 to the tissue receiving configuration. Once the target tissue has been received between the clip arms 110, the clip assembly 102 may be moved toward the tissue gripping configuration so that the target tissue is gripped between the distal ends 118 thereof. The clip arms 110 are moved toward the tissue gripping configuration by drawing the control member 114 proximally with respect to the catheter 138 and the capsule 120. Once the clip assembly 102 is in the tissue gripping configuration, the control member 114 may be drawn further proximally to lock the clip arms 110 with respect to the capsule 120.

To deploy the clip assembly 102, the control member 114 is drawn even further proximally until a force exerted on the connector 116 via the distal end 112 of the connector 114 exceeds the predetermined threshold value, separating the proximal portion 124 of the connector 116 from the distal portion 126 thereof, as shown in FIG. 5. Upon separation of the proximal portion 124, and thereby the control member 114, from the clip arms 110, the control member 114 may be moved distally to press the proximal portion 124 distally against the distal portion 126 until a force exerted thereon exceeds a predetermined threshold value to disengage the capsule 120 from the catheter 138. Once the capsule 120 has been separated from the catheter 138, the applicator 104 may be withdrawn proximally from the body, leaving the clip assembly 102 clipped over the target tissue. The proximal portion 124 of the connector 116 and the malleable element 106, which remain connected to the control member 114, may be removed therefrom by rotating the malleable element 106 relative to the control member 114 so that the malleable element 106 is disengaged from the threading 148 thereof. If so desired, a new clip assembly 102 is then loaded onto the applicator 104, in the same manner as described above, so that the device may then be used to clip a second portion of tissue. This process may be repeated using the same applicator 104 as many times as needed or desired.

Figure 10:
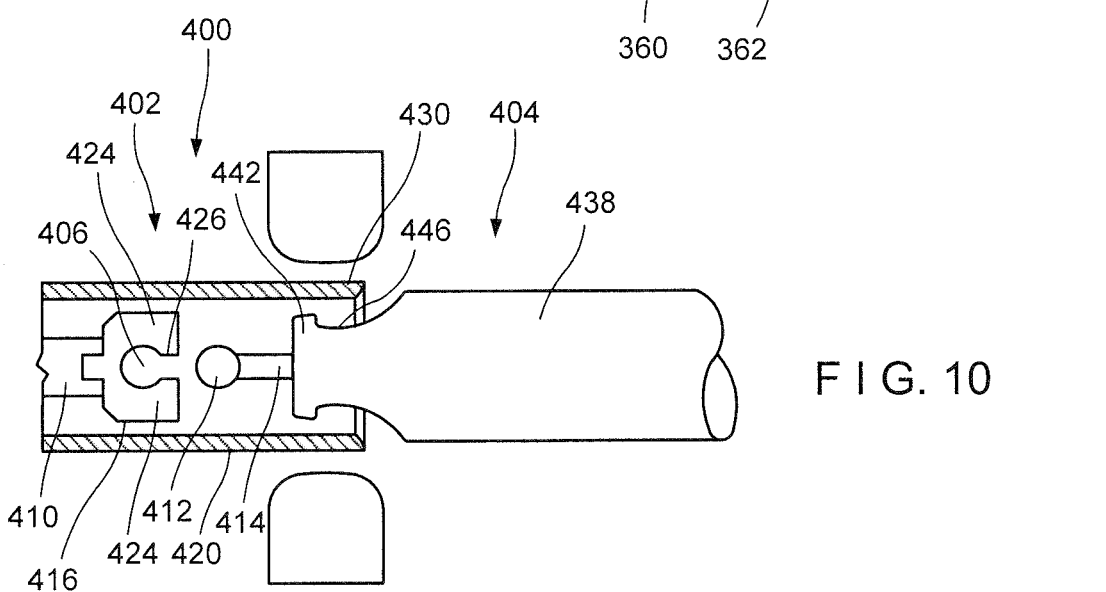
FIG. 10 shows a partially cross-sectional longitudinal side view of a system according to another exemplary embodiment of the present disclosure, in an unloaded configuration.
Figure 11:
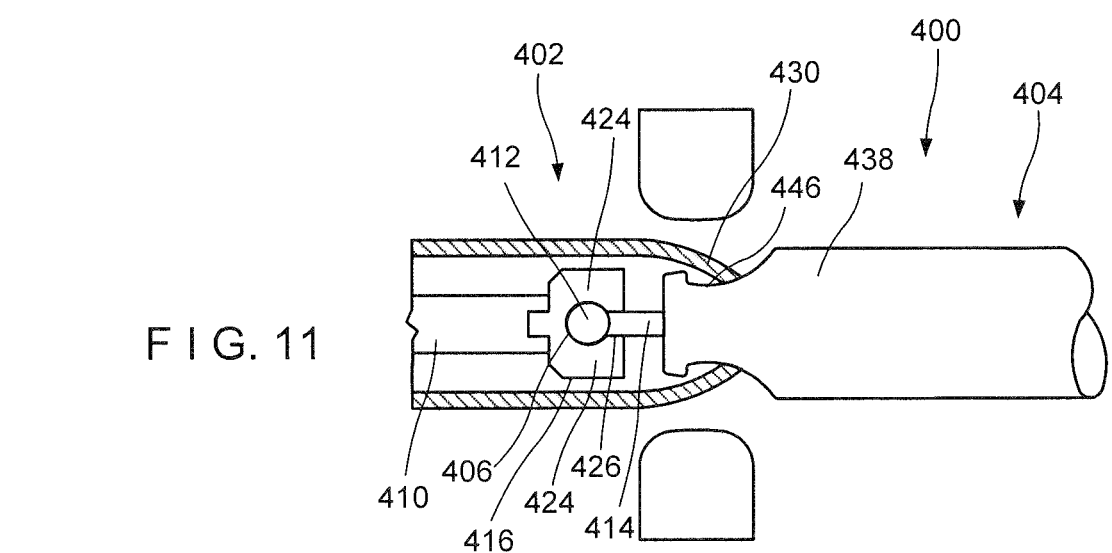
FIG. 11 shows a partially cross-sectional longitudinal side view of the system of FIG. 10, in a loaded configuration.

As shown in FIGS. 10-11, a system 400 according to another exemplary embodiment of the present disclosure is substantially similar to the system 100 described above, comprising a clip assembly 402 loadable onto a distal portion of an applicator 404. The clip assembly 402 is substantially similar to the clip assembly 102, described above, comprising clip arms 410, proximal ends of which are slidable within a capsule 420 to move the clip assembly 402 between an open, tissue receiving configuration and a closed, tissue gripping configuration. Rather than a malleable element for connecting the clip arms 410 to a control member 414, however, the proximal ends of the clip arms 410 are connected to a yoke 416. The yoke 416 includes a socket 406 sized and shaped to releasably receive an enlarged distal end 412 of the control member 414. The yoke 416 of this embodiment includes opposed portions 424 defining a proximal opening 426 and the socket 406. A cross-sectional area of the proximal opening 426 is smaller than a cross-sectional area of the socket 406. The opposed portions 424 of this embodiment are spreadable to receive the enlarged distal end therepast and biased so that, once the enlarged distal end passes the proximal opening 426 and enters the socket 406, the opposed portions 424 spring back to lock the enlarged distal end 412 therein.

The applicator 404 may be substantially similar to the applicator 104, described above, comprising a bushing 438 or catheter at a distal end thereof and the control member 414 extending therethrough. A distal end 442 of the bushing 438, however, includes an engagement feature 446 configured as, for example, a cut out extending laterally into or, in this embodiment, through a wall of the capsule 420 at the distal end 442 so that the cut out is in communication with a lumen extending longitudinally through the bushing 438. In this embodiment, a proximal end 430 of the capsule 420 may be crimped over the distal end 442 of the bushing 438 such that the proximal end 430 of the capsule 420 is crimped into the cut out so that the proximal end 430 of the capsule 420 extends into the lumen of the bushing 438. Thus, the capsule 420 is engaged to the bushing 438. Upon coupling the control member 414 to the yoke 416 and coupling the capsule 420 to the bushing 438, the control member 414 may be moved longitudinally relative to the bushing 438 to move the clip assembly 402 between the tissue receiving and the tissue gripping configurations.

When target tissue has been clipped as desired, the control member 414 may be drawn proximally until the clip arms 410 are locked relative to the capsule 420 to lock the clip assembly 402 in the tissue gripping configuration. In this configuration, the yoke 416 is drawn into the distal end 422 of the bushing 438 over which the capsule 420 is crimped. As the yoke 416 is drawn into the bushing 438, the yoke 416 contacts the crimped portion of the capsule 420 (e.g., the portion of the capsule 420 extending through the cut out), pushing the crimped portion of the capsule 420 out of the lumen of the bushing 438 so that the capsule 420 is disengaged from the bushing 438. Since the clip assembly 402 is locked in the tissue gripping configuration (i.e., the clip arms 410 are locked with respect to the capsule 420), any further proximal motion of the control member 414 causes the enlarged distal end 412 of the control member 414 to exert a proximal force on the yoke 416. The control member 414 is drawn proximally until a force exerted on the yoke 416 exceeds a predetermined threshold value, causing the distal end 412 to be released from the yoke 416. The applicator 404 may then be removed from the body, leaving the clip assembly 402 clipped over a target tissue in the body.

According to another exemplary embodiment, as shown in FIGS. 12-13, a system 500 may be substantially similar to the system 100 described above, comprising a clip assembly 502 loadable onto a distal portion of an applicator 504. The applicator 504 may be substantially similar to the applicator 104 described above, comprising a catheter 538 through which a control member 514 having an enlarged distal end 512 extends. The clip assembly 102 is also substantially similar to the clip assembly 102. Rather than a malleable element, however, the clip assembly 502 comprises a connector 516 connected to proximal ends 508 of clip arms 510, the connector 516 configured to be coupled to the enlarged end 512 of the control member 514. The connector 516 includes a proximal portion 524 and a distal portion 526 connected to one another via a separable link 522. The proximal portion 524 includes a pair of components 506 movable relative to one another between a non-engaging configuration, in which the pair of components 506 are separated from one another to receive the enlarged end 512 of the control member 514 therein, and an engaging configuration, in which the pair of components 506 are moved toward one another to hold the enlarged distal end 512 therein. The pair of components 506, when in the engaging configuration, define a space 525 therebetween sized and shaped to hold the distal end 512. The pair of components 506 include corresponding snap features 548 which hold the pair of components 506 in the engaging configuration when the snap features 548 are engaged with one another. The capsule 520 and the catheter 538 may be coupled to one another in a manner substantially similar to the capsule 120 and the catheter 138 described above with reference to the system 100.

The pair of components 506 may include tapered surfaces 523 tapering toward the separable link 522. The tapered surfaces 523 of the pair of components 506 interface with a correspondingly tapered surface 533 along a proximal portion of a lumen 532 of the capsule 520 to move the pair of components from the non-engaging configuration to the engaging configuration. In other words, as the tapered surfaces 523 of the pair of components 506 slide along the tapered surface 533 of the capsule 520, the pair of components 506 are drawn together toward the engaging configuration, to hold the enlarged distal end 512 of the control member 514 therein. A distal insertion of the enlarged end 512 into the space 525 between the separated components 506 in the non-engaging configuration will push the pair of components distally against the capsule 520, moving the pair of components 506 toward the engaging configuration.

The separable link 522 of the connector 516 may be configured as, for example, a notch extending about the connector 516 to connect the proximal portion 524 and the distal portion 526 of the connector 516 to one another. The notch is configured to weaken the connector 516 at this position so that it will break, separating the proximal and distal portions 524, 526 when a force exerted thereon exceeds a predetermined threshold value. Although the separable link 522 is shown and described as a notch, the separable link 522 may have any of a variety of configurations, so long as the link is separated when a force exerted thereon exceeds the predetermined threshold value, thereby separating the proximal and distal portions 524, 526 of the connector 516.

Once the clip assembly 502 has been used to grip a target tissue, as desired, the clip assembly 502 may be locked in a tissue gripping configuration, in substantially the same manner as described above with respect to the system 100. In particular, the control member 514 is drawn proximally until locking features of the clip arms 510 engage a corresponding locking feature of the capsule 520. Upon locking of the clip arms 510 relative to the capsule 520, the control member 514 may be drawn even further proximally to deploy the clip assembly 502. The control member 514 is drawn proximally until a force exerted on the connector 516 exceeds a predetermined threshold value, causing the separable link 522 to break and/or release to separate the proximal and distal portions 524, 526. Thus, the distal portion 526 will remain connected to the clip assembly 502 while the proximal portion 524 may be removed from the body along with the control member 514 and the catheter 538, leaving the clip assembly 502 clipped over a target tissue in the body. Once the applicator 504 has been removed from the body, the proximal portion 524 of the connector 516 may be manually removed from the enlarged distal end 512 of the control member 514 so that the same applicator 504 may be reloaded with a new clip assembly 502, as desired.

It will be apparent to those skilled in the art that various modifications may be made in the present disclosure, without departing from the scope of the disclosure. For example, any of the features or elements of one embodiment may be combined with any other embodiment disclosed herein unless the combination is in any way contradicted by the disclosure of this application.

What is claimed is:

1. A system for treating tissue, comprising:
    an applicator including a catheter extending longitudinally from a proximal end to a distal end and including a lumen extending therethrough, a control member extending through the lumen of the catheter; and
    a plurality of clip assemblies, each clip assembly being releasably coupleable to a distal end of the applicator and including a pair of clip arms, proximal ends of which are slidably received within a channel of a capsule, a pair of opposing coupling elements extending proximally from the proximal ends of the clip arms to be fixed over the distal end of the control member so that the clip arms are movable relative to the capsule via a longitudinal motion of the control member between a tissue receiving configuration, in which distal ends of the clip arms are separated from one another, and a tissue clipping configuration, in which distal ends of the clip arms are moved toward one another, wherein each clip assembly, after deployment, is separable into a distal portion including the clip arms that remain clipped over target tissue and a proximal portion including the coupling elements that remain removably coupled to the control member so that, after removal of the separated proximal portion from the control member, a new clip assembly may be coupled to the control member, wherein the opposing coupling elements include malleable sheets crimped over the distal end of the control member.

2. The system of claim 1, wherein the distal end of the control member includes a threading extending therealong.

3. The system of claim 1, wherein the proximal ends of the clip arms are connected to one another via a connector including a proximal portion and distal portion connected to one another via a frangible link designed to fail when a predetermined threshold force is exerted thereon, a malleable element extending proximally from the proximal portion.

4. The system of claim 3, wherein the frangible link is configured as a notch extending about the connector between the proximal and distal portions.

5. The system of claim 1, wherein a proximal end of the capsule is releasably coupleable to a distal end of the catheter.

6. The system of claim 5, wherein the proximal end of the capsule includes a protrusion extending laterally outward from an exterior surface thereof and the distal end of the catheter includes a correspondingly sized and shaped recess extending along an interior surface of the lumen, the protrusion configured to be snap fit in the recess.

7. The system of claim 1, wherein the clip arms are biased in the tissue receiving configuration so that, when the clip arms are drawn proximally into the capsule, an interior surface of the capsule constrains the clip arms toward the tissue gripping configuration.

8. The system of claim 1, further comprising a cartridge defining a space therewithin for housing the clip assembly.

9. The system of claim 8, wherein the cartridge includes a crimping mechanism including crimping members coupled to the cartridge so that a portion of the crimping members are movable toward one another to crimp the opposing coupling elements over the control member.

10. The system of claim 8, wherein the space of the cartridge is defined via a tapered surface engaging the opposing coupling elements when the clip assembly is moved distally relative thereto so that the opposing coupling elements are moved toward the control member to be crimped thereover.

11. The system of claim 1, wherein the pair of opposing coupling elements define a space sized and shaped to receive an enlarged distal end of the control member, the opposing coupling elements movable between a non-engaging configuration, in which the opposing coupling elements are separated from one another to receive the enlarged distal end therebetween, and an engaging configuration, in which the opposing coupling elements are moved toward one another to fix the enlarged distal end therein, the pair of opposing coupling elements including corresponding snap features for releasably locking the opposing coupling elements in the engaging configuration.

12. The system of claim 11, wherein the capsule includes an angled surface along a proximal end of the channel, the angled surface configured to interface with tapered surfaces of the opposing coupling elements to move the opposing coupling elements from the non-engaging configuration toward the engaging configuration.

13. A system for treating tissue, comprising:
an applicator including a bushing and a control member extending therethrough, the bushing including an engagement feature at a distal end thereof; and
a plurality of clip assemblies, each clip assembly being releasably coupleable to a distal end of the applicator and including a pair of clip arms, proximal ends of which are slidably received within a channel of a capsule, proximal ends of the clip arms configured to be connected to a distal end of the control member and a proximal end of the capsule configured to be crimped over the engagement feature of the bushing so that the clip arms are movable relative to the capsule between a tissue receiving configuration, in which distal ends of the clip arms are separated from one another, and a tissue clipping configuration, in which distal ends of the clip arms are moved toward one another, via a longitudinal motion of the control member relative to the bushing, each clip assembly, after deployment, being separable from the bushing leaving the clip arms clipped over target tissue so that the applicator and the bushing may be withdrawn from the body and a new clip assembly may be coupled to the applicator.

14. The system of claim 13, wherein the proximal ends of the clip arms are connected to one another via a yoke including a socket sized and shaped to releasably receive an enlarged distal end of the control member.

15. A method for treating tissue, comprising:
loading a first clip assembly on an applicator by coupling a control member of the applicator to proximal ends of clip arms of the first clip assembly by crimping a malleable element connected to the proximal ends of the clip arms over a threaded distal end of the control member and by coupling a catheter of the applicator to a proximal end of a capsule of the first clip assembly;
inserting the loaded first clip assembly to a target site within a living body via a working channel of an endoscope;
moving the clip assembly between a tissue receiving configuration, in which distal ends of the clip arms are separated from one another, and a tissue clipping configuration, in which distal ends of the clip arms are moved toward one another, by moving the control member longitudinally relative to a locking sleeve until a target tissue is gripped therebetween, as desired; and
releasing the first clip assembly from the applicator by drawing the control member proximally relative to the first clip assembly, beyond a predetermined threshold value, so that a malleable element separates from the proximal end of the clip arms.

16. The method of claim 15, further comprising locking the clip assembly in the tissue clipping configuration such that the target tissue is locked between the clip arms.

17. The method of claim 15, wherein releasing the first clip assembly from the applicator further comprises pushing the control member distally against the first clip assembly so that the capsule is disengaged from the catheter.

18. The method of claim 15, further comprising withdrawing the applicator from the body, leaving the first clip assembly clipped over the target tissue in the body and unthreading the malleable element from the threaded distal end of the control member.

19. The method of claim 15, further comprising loading a second clip assembly on the applicator by coupling the control member of the applicator to proximal ends of clip arms of the second clip assembly by crimping a malleable element connected to the proximal ends of the clip arms of the second clip assembly over the threaded distal end of the control member and by coupling a catheter of the applicator to a proximal end of a capsule of the second clip assembly.

* * * * *